(12) United States Patent
Woo (10) Patent No.: US 6,753,537 B2
(45) Date of Patent: Jun. 22, 2004

(54) PORTABLE TOOTHBRUSH CASE WITH UV LAMP

(76) Inventor: Jin-Ho Woo, #103-303, Hyundae Apt., 307, Sankok-Dong, Boopyung-Gu, Inchun-City (KR)

( * ) Notice: Subject to any disclaimer, the term of this patent is extended or adjusted under 35 U.S.C. 154(b) by 0 days.

(21) Appl. No.: 10/341,688

(22) Filed: Jan. 13, 2003

(65) Prior Publication Data

US 2004/0089815 A1 May 13, 2004

(30) Foreign Application Priority Data

Nov. 7, 2002 (KR) .......................................... 2002-68628
Nov. 18, 2002 (KR) .......................................... 2002-71480

(51) Int. Cl.[7] .......................... G01N 23/00; G01N 21/00; H01J 37/20
(52) U.S. Cl. .............................. 250/455.11; 250/453.11; 250/454.11
(58) Field of Search .................................... 250/455.11

(56) References Cited

U.S. PATENT DOCUMENTS

| 4,906,851 A | * | 3/1990 | Beasley et al. | ........ 250/455.11 |
| 5,852,879 A | * | 12/1998 | Schumaier | ...................... 34/80 |
| 6,099,813 A | | 8/2000 | Gipson, II | .................. 422/300 |

FOREIGN PATENT DOCUMENTS

JP 11-318566 11/1999

* cited by examiner

Primary Examiner—John R. Lee
Assistant Examiner—Erin-Michael Gill
(74) Attorney, Agent, or Firm—Ladas & Parry (57) ABSTRACT

The invention relates to a toothbrush case, the toothbrush case comprising a lower case having a projection portion for projecting at a given height (T) on a supporting surface, a ultraviolet radiation source supported by the supporting surface in the lower case, a receiving member having a portion for receiving the toothbrush so that it can sanitize the toothbrush with ultraviolet light, and an upper case being hinge coupled with the lower case for opening and closing the receiving member, the toothbrush case further comprising: a spaced supporting portion being provided in the lower surface of the supporting surface in the lowercase and being projected at the given height (T) so that moisture in the ground such as a bathroom's ground are not in contact with the supporting surface and that outside air flows into the bottom of the supporting surface in the case that the lower case is placed on the ground, a lower air flow path being formed on the surface of the supporting surface in the lower case so that outside air through a space created by the spaced supporting portion flows into the inside of the lower case; an air flow path provided between the ultraviolet radiation means and the ultraviolet discharging outlet of the receiving member so that outside air flows through the lower air flow path into the sealing space between the receiving member and the upper case; and an upper airflow path provided on the upper case so that outside air flows through the upper case into the receiving member having the air flow path.

11 Claims, 12 Drawing Sheets

PORTABLE TOOTHBRUSH CASE WITH UV LAMP

CROSS-REFERENCE TO RELATED APPLICATIONS

This application claims the benefit of Korean Application No. 2002-68628, filed Nov. 07, 2002 and Korean Application No. 2002-71480, filed Nov. 18, 2002, in the Korean Intellectual Property Office, the disclosure of which is incorporated herein by reference.

BACKGROUND OF THE INVENTION

Field of the Invention

The present invention relates to a toothbrush case having an ultraviolet (UV) radiation means therein which can sterilize the toothbrush by using UV light, thus keeping the toothbrush with sterilization status, particularly to the toothbrush case which can promote sterilization power by radiating more active UV light to the toothbrush bristles, can minimize power consumption by radiating UV light to the bristles at the proper time period, and can grip the toothbrush case easily even if the toothbrush case is positioned on a mist place, such as a bathroom's ground.

In general, the toothbrush is received in a separate toothbrush case, a receptacle or so.

Current medical research indicates that the toothbrush is a major contributor to the spread of colds and diseases because the toothbrush bristles are contaminated with dirt, filth and bacteria, yet the toothbrush is a necessary tool in the preservation of teeth and gums.

In order to prevent contamination of the toothbrush bristles, various types of the toothbrush cases have been proposed all over the world.

U.S. Pat. No. 6,099,813 to Gipson II discloses an example of such a toothbrush case.

Figure 1:
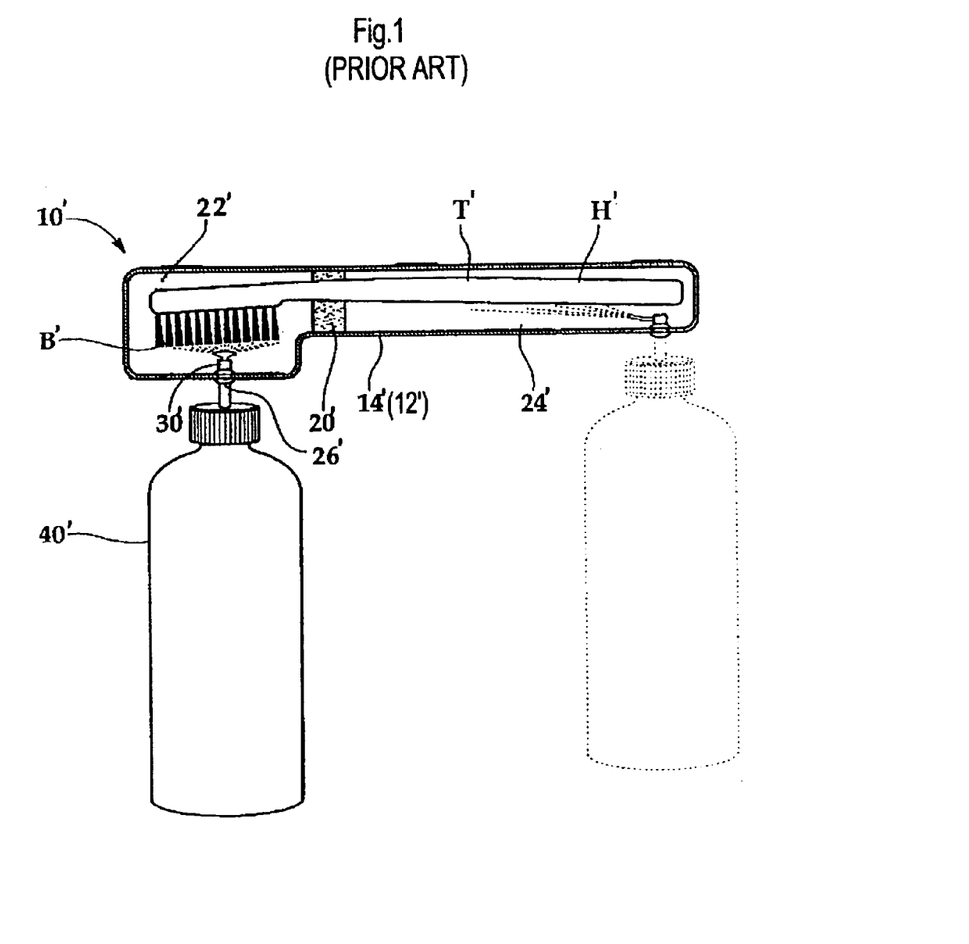
FIG. 1 is a status diagram showing the toothbrush holder and sanitizer case according to the U.S. Pat. No. 6,099,813 of the prior art.

The '813 patent as illustrated in FIG. 1 discloses a case for holding and sterilizing a toothbrush T' comprising; a first side 12'; a second side 14', said first and second sides 12' and 14' being capable of a mating fit to form a fluid-tight container capable of holding a toothbrush T'; a fluid seal 20' in said first and second sides 12' and 14', whereby, when said sides 12' and 14' are mated, said case 10' is divided into a first isolated chamber 22' for receiving the toothbrush bristles B' and a second isolated chamber 24' for receiving the toothbrush handle H'; a port 26' in said case 10' to permit fluid communication from outside said case 10' into said isolated bristle chamber; and a unidirectional flow valve 30' in said port 26' to permit one-way fluid flow into said isolated chamber 22'.

The toothbrush holder and sanitizer case of the '813 patent as mentioned above has an effect which can use the toothbrush sanitarily by sterilizing the toothbrush contained within the case by using a pressurized aerosol can 40' connected to a port 26', in order to use the toothbrush sanitarily.

However, the toothbrush holder and sanitizer case of '813 patent have disadvantages such that they are inconvenient to use and not easy to keep because both the case and the pressurized aerosol must be contained together.

On the other hand, in Japan various types toothbrush cases are proposed to sterilize the toothbrush bristles by using UV light and have convenient portability.

As an example of such a prior art, Japanese patent Laid-Open No. 11-318566(Nov. 24, 1999) discloses a portable sterilizing apparatus, which can sterilize the toothbrush's bristle by using a UV light.

Figure 2:
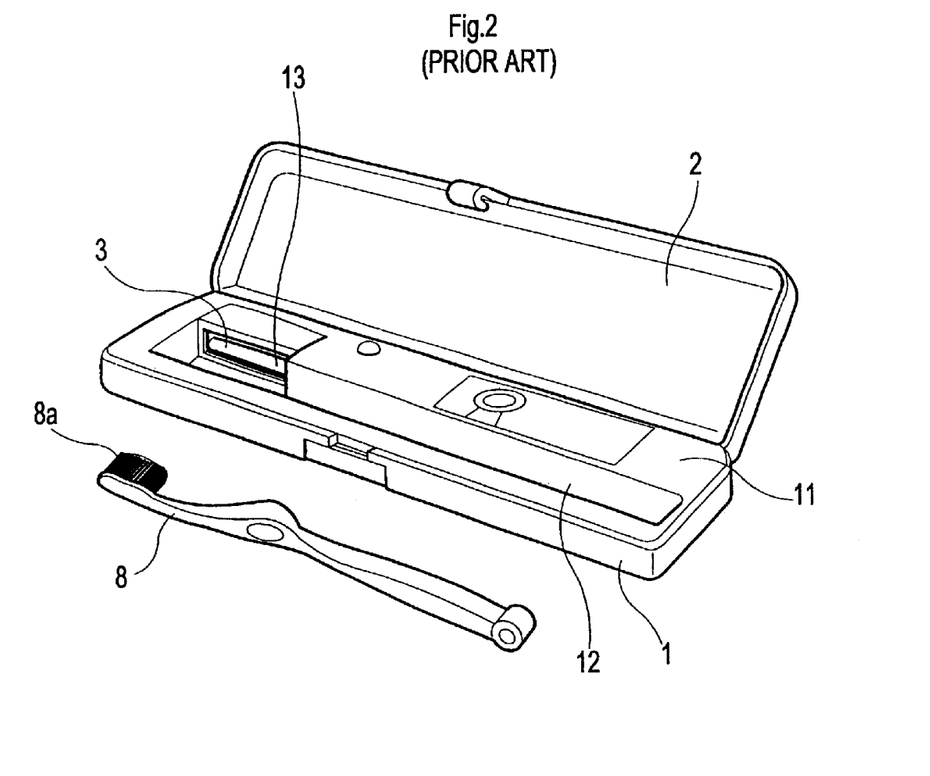
FIG. 2 is a perspective view showing the toothbrush case according to the Japan patent Laid-Open No. 11-318566 of the prior art.

The apparatus as shown in FIG. 2 comprises a cover member 2 for opening and closing freely provided on an upper surface of a case body 1, a tray 11 for receiving a toothbrush 8 removably provided within the case body 1, an UV sterilizing lamp 3 for irradiating UV light to the brush portion 8a of the toothbrush 8, and a switch for detecting the opening and closing of the cover 2, a receiving concave 12 adoptive to shape of the toothbrush 8 being provided in the tray 11, the concave 12 being provided with a opening member 13 in the position corresponding to brush portion 8a of toothbrush 8, the lamp turning on the lamp for a given period time when the switch turning on and irradiating the UV light to the brush portion through the opening.

According to such a portable sterilizing apparatus, if the cover is closed, with the toothbrush 8 being received within the concave 12 of the tray 11, the UV light are irradiated from the lamp 3, whereby it is possible to sterilize bacteria penetrated to the brush portion 8a of the toothbrush 8.

However, according to Japan patent Laid-Open No. 11-318566, one disadvantage is that if the cover 2 is closed, space within the tray 11 is sealed completely, generating moisture excessively in space within the tray 11 due to moisture left in the brush portion 8a.

Also, since moisture is remained in the brush portion 8a, if fog is generated on the surface of the cover member 2 and the tray 11, outer appearance of the case will be dirtied, and fog dew is generated on the UV lamp 3, thereby reducing the intensity of UV radiated from UV lamp 3. It is impossible to sterilize the brush portion 8a of the toothbrush 8 effectively.

Also, in case that the portable sterilizing apparatus is positioned in a wet place such as bathroom's ground, the apparatus will fail because moisture can be penetrated into the battery if body 1 has a simple planar structure. Moreover, it is not easy to pick up the toothbrush case from a wet place, such as the ground of a bathroom, due to surface tension.

Another disadvantage is that the apparatus consumes power excessively by keeping the UV lamp 3 continuously active when the cover member 2 is closed, The UV radiation toothbrush cases in the prior art have disadvantages as follows. Moisture is left in the toothbrush bristles and generated inside the toothbrush case. Thus, the UV radiation toothbrush case can not sterilize the bristles effectively because the intensity of UV light is reduced by moisture. Also, in case that the toothbrush case is placed in a wet place, the toothbrush case is likely to fail because moisture is penetrated into the inside of the case. Also it is not easy to pick up the case due to the surface tension occurring between the case and the bottom surface, where the case is positioned. The prior art UV radiation toothbrush case can spend power excessively because the UV sterilizing lamp remains active when the cover is closed.

SUMMARY OF THE INVENTION

Accordingly, it is an objective of the present invention to provide a toothbrush case which has a good appearance by preventing moisture from generating in the inside of the case, and which can sterilize the toothbrush more effectively without reduction of the intensity of UV.

It is another objective of the present invention to provide a toothbrush case, which can prevent cause of failure in advance by preventing moisture from penetrating into the inside of the toothbrush case and which can be picked up easily even if the case is placed in a wet place such as the bathroom's ground.

It is another objective of the present invention to provide a toothbrush case which can minimize power consumption by turning on the UV radiation means with proper timing.

The foregoing objectives can be accomplished in one embodiment by providing a toothbrush case comprising a lower case having a projection portion for projecting at a given height (T) on a supporting surface, an UV radiation means supported by the supporting surface in the lower case, a receiving member having a portion for receiving the toothbrush so that can sanitize the toothbrush with UV light radiated by the UV radiation means, and an upper case being coupled by hinge with the lower case for opening and closing the receiving member, the toothbrush case further comprising: a spaced supporting portion being provided in the lower surface of the supporting surface in the lowercase and being projected at the given height (T) so that moisture in the ground such as a bathroom's ground does not contact with the supporting surface as well as outside air flowing into the bottom of the supporting surface in case that the lower case is placed on the ground; a lower air flow path being formed on the surface of the supporting surface in the lowercase so that outside air through a space spaced from the ground by the spaced supporting portion flows into the inside of the lower case; air flow path provided between the UV radiation means and the UV discharging outlet of the receiving member so that outer inflow air flowed into the lower air flow path flows in the sealing space by the receiving member and the upper case; and an upper air flow path provided on the upper case so that outside air flows through the upper case into the receiving member having the air flow path.

According to the toothbrush case of the present invention, the vapor generating due to the moisture left in the bristle of the toothbrush is exhausted to the outside of the case through the upper air flow path in the upper case and the lower case air flow path in the lower case, preventing from generating fog in the inside of the case. Also it is possible to prevent the penetration of moisture into the lower case by the spaced supporting portion formed into the lower case, and to prevent cause of failure in advance.

BRIEF DESCRIPTION OF THE SEVERAL VIEWS OF THE DRAWING

A preferred embodiment of the invention will now be described with reference to the FIGURES.

In FIG. 3 to FIG. 12, the numeral 100 indicates a toothbrush with a toothbrush bristles 110, and the numeral 20 indicates a lower case having a projecting portion 22 protruded in a given height T from a supporting surface 21.

A lower projecting portion 23 is protruded on the front surface of the projecting portion 22 in the lower case 20 so that the upper case, as will be described in detail below, can be opened and closed easily by hand, and a hinge projection 24 is projected on the both rear side of the projection 22.

Figure 5:
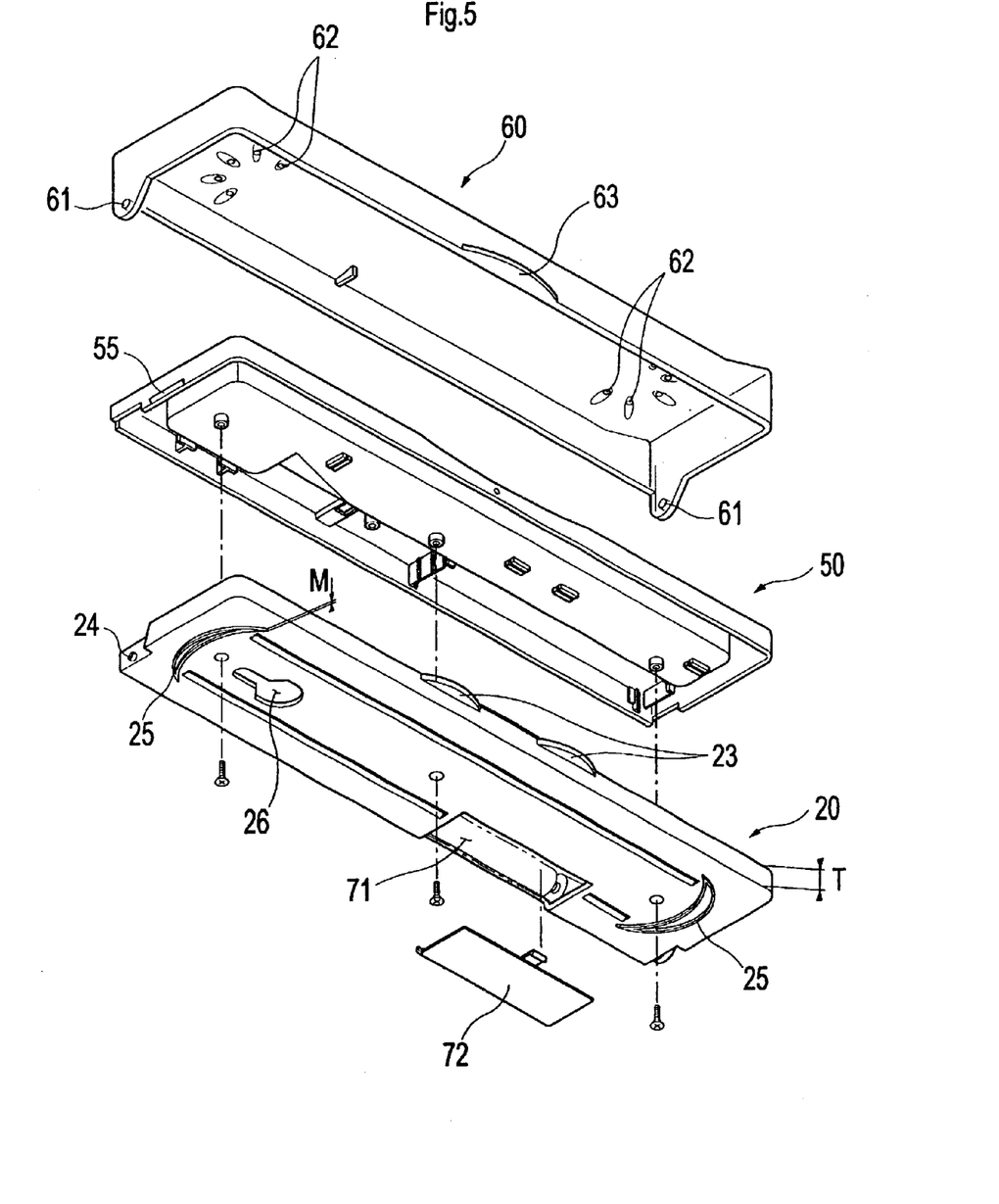
FIG. 5 is an exploded perspective view showing main components of the toothbrush case according to the present invention taken from a lower part.
Figure 7:
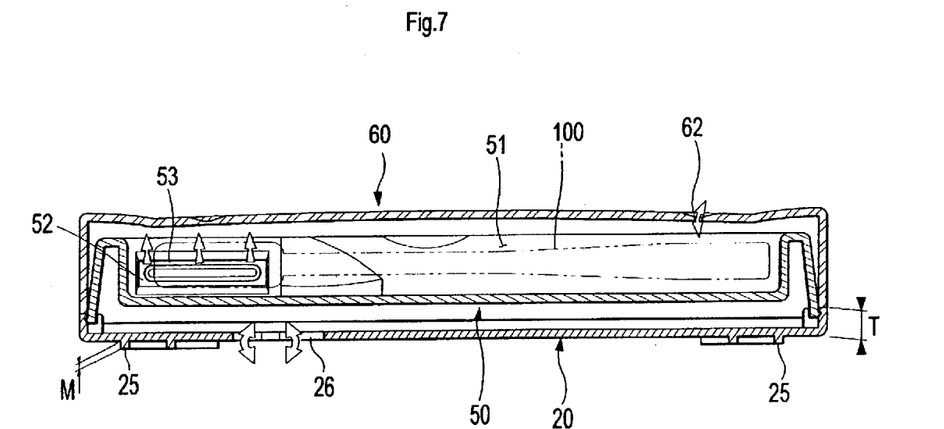
FIG. 7 is a sectional view taken along line A—A of FIG. 3.

As shown in FIG. 5 and FIG. 7, a spaced supporting portion 25 is formed at a given height M on both side of the lower surface of the supporting surface 21 in the lower case 20 so that the supporting surface 21 is maintained at a given spaced distance from the ground, and by this supporting portion, the surface 21 is out of contact with moisture remained in the ground as well as air flows through a lower air flow path as will be described below in case that the lower case 20 is placed on the ground such as bathroom's ground.

The lower airflow path 26 is formed on the supporting surface 21 having the spaced supporting part 25. By this air flow path, even if the lower case 20 is placed on the ground such as bathroom's ground, outside air due to the space spaced from the ground may flow into the inside of the lower case 20, and the air flow path serve to a member for hanging the lower case 20 to a member such as nail.

An engagement groove 27 is formed on both of the inside surface of the projection portion 22 in the lower case 20 in order to be engaged with a receiving member as will be described below easily and fixedly.

A plurality of supporting projecting portions 28 is formed on the inside of the projection portion 22 of the lower case 20 so that the receiving member is hold into a securely engaged state.

A portion 71 for receiving batteries is formed on the supporting surface 21 of the lower case 20. The receiving portion 71 is opened or closed by a cover member 72.

The supporting surface 21 is provided with an UV radiation means 30 for radiating UV light to sterilize the bristles 110 of the toothbrush 100 by UV light.

Figure 6:
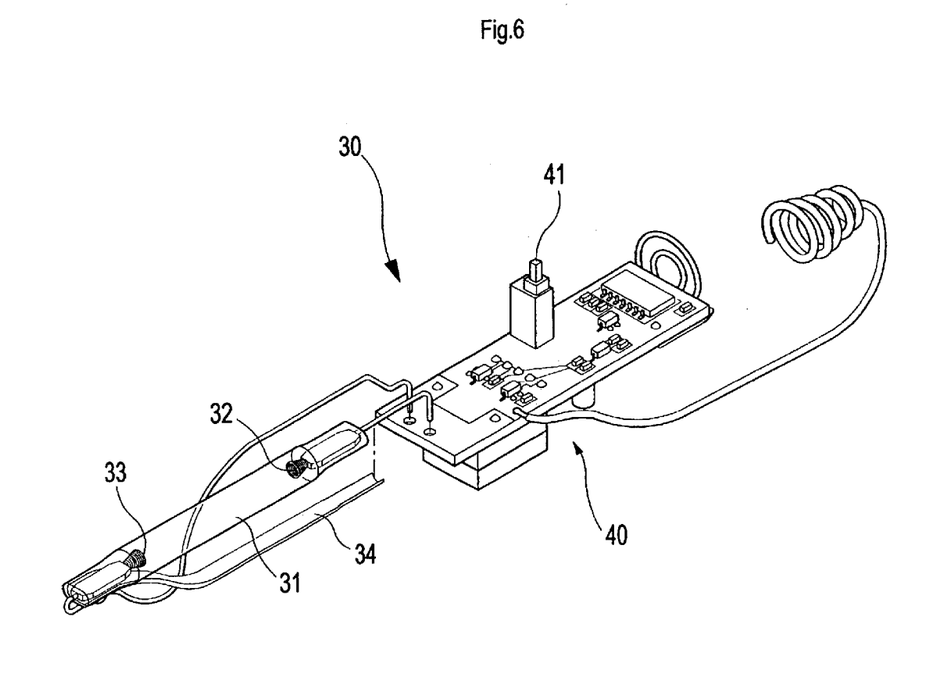
FIG. 6 is a perspective view showing UV radiation means in the toothbrush case according to the present invention.

As shown in FIG. 6, the UV radiation means 30 comprises a lamp 31 made of a transparent crystal material having high transmissivity, the lamp being sealed with gas mixed with inert gas such as Hg and Ar; a first and a second W filament coils 32 and 33 provided on the both end of the lamp emitting hot electrons, the coils being coated with BaO2 thereon so that hot electrons can be emitted easily by gas mixed within the lamp 31; a condenser 34 made of high conductive material such as a thin Cu plate, one end of the condenser coupled to the second W filament coil 33, and the other end of the condenser coupled to the top of the first W filament coil 32 to discharge gas by hot electron emission of gas even if a low voltage is applied to the first and the second W filament coil 32 and 33; and a control member 40 for controlling hot electron emission and UV radiation light by the condenser 34 under the low voltage.

Namely, in case that the low voltage is applied initially to the toothbrush case under control of the control member 40, the voltage is applied to the condenser member 34, one end of the condenser being coupled to the second W filament coil 33, and the other end of the condenser being coupled to the top of the first W filament coil 32 so that UV light is emitted from the lamp 31 by discharging gas mixed between the condenser member 34 and the first W filament coil 32.

The control member 40 controls UV light radiated from the lamp 31 to sterilize the toothbrush 100 effectively.

The control member 40 comprises a sensor 41 for detecting when the toothbrush 100 is positioned in the case and the upper case is closed; a power supply 42 for supplying power supplied by a detecting signal of sensor 41; a controller 43 for controlling power from the power supply 42 in power saving mode; a voltage output part 44 for supplying regularly a voltage supplied from the power supply 42 to the W filament coils 32 and 33.

Figure 11A:
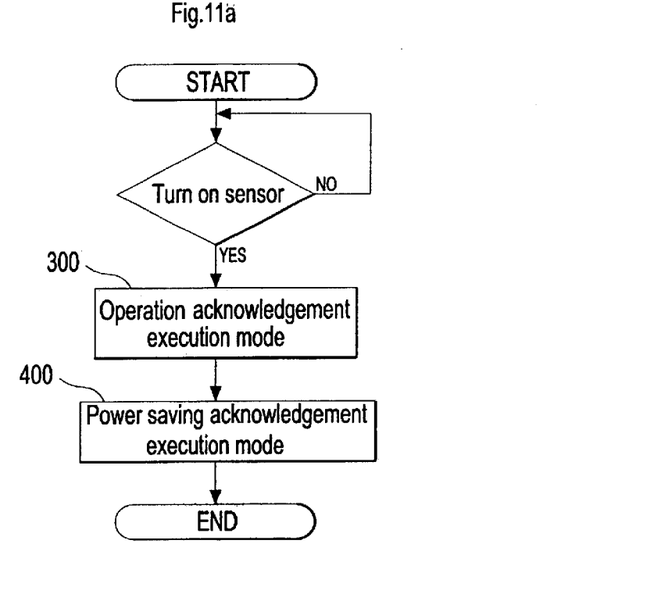
FIG. 11 is a flow chart illustrating operational order of radiation means in the toothbrush case according to the present invention.
Figure 11B:
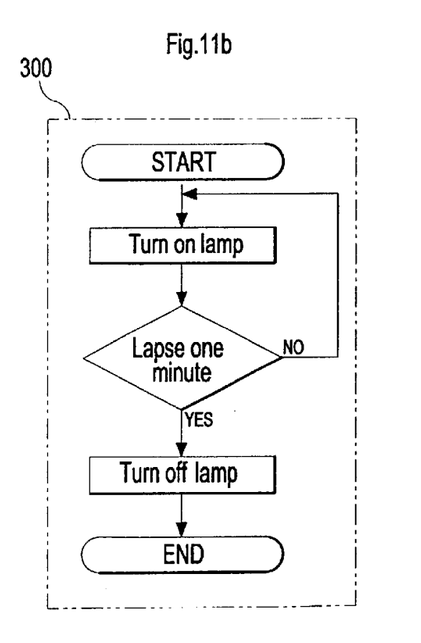
Figure 11C:
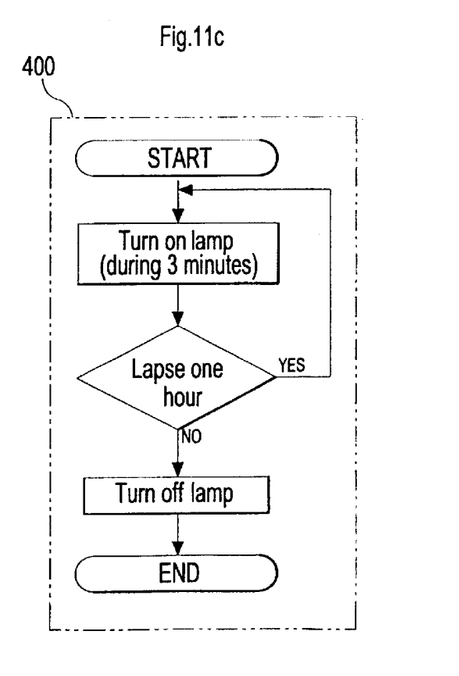

The control member 40 can operate with an operation acknowledgement execution mode 300 and a power saving acknowledgement mode 400 as shown in FIG. 11 so that UV light can be radiated in the power saving mode.

The control member 40 can operate with an operation acknowledgement execution mode 300 for turning on the lamp 31 during one minute, then for turning off it in order to capture whether lamp 31 operates correctly or not, and a power saving acknowledgement mode 400 for turning on the lamp 31 for three minutes each hour in the power saving mode after the operation acknowledgement execution mode 300 is executed in order to radiate UV light effectively in the power saving mode.

The numeral 50 is a member for receiving the toothbrush 100 and having an UV discharging outlet 52 which radiates UV radiating from the UV radiation means 30 to the toothbrush 100, the receiving member having a receiving portion 51 and being engaged with the lower case 20.

An air flow path 53 is formed between the UV discharging outlet 52 and the UV radiation means 30 as shown in FIG. 7 which allows outside air flowing in the lower air flow path 26 and allows outside air flowing in an upper air flow path as will be described below.

The receiving member 50 is injection molded with photocatalyst such as TiO2 which can eliminate a bad smell, bacteria, and mold by a strong oxidation-reduction reaction resulting from the UV light radiated by the UV radiation means 30 responsive to an ambient organic material, or is coated by spraying photocatalyst such as TiO2 onto an antimicrobial ABS resin.

Figure 8:
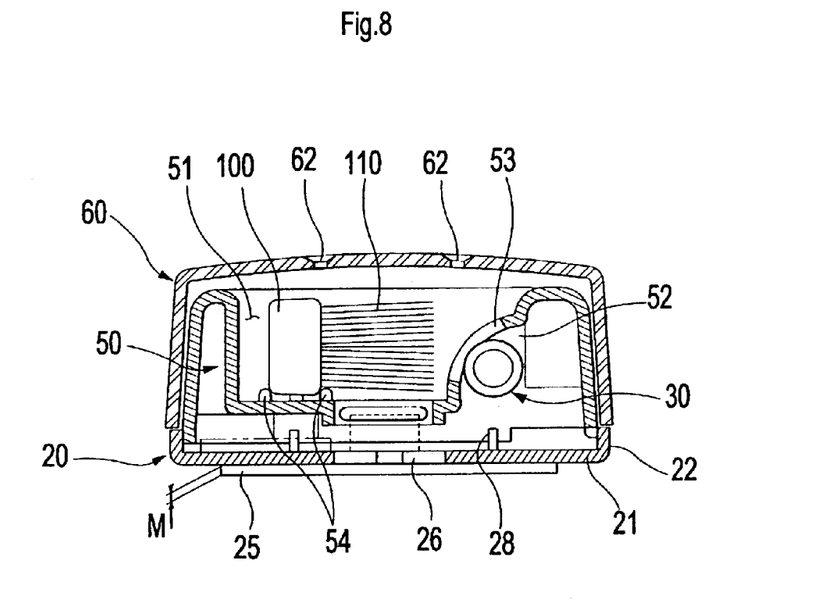
FIG. 8 is a sectional view taken along line B—B of FIG. 3.
Figure 9:
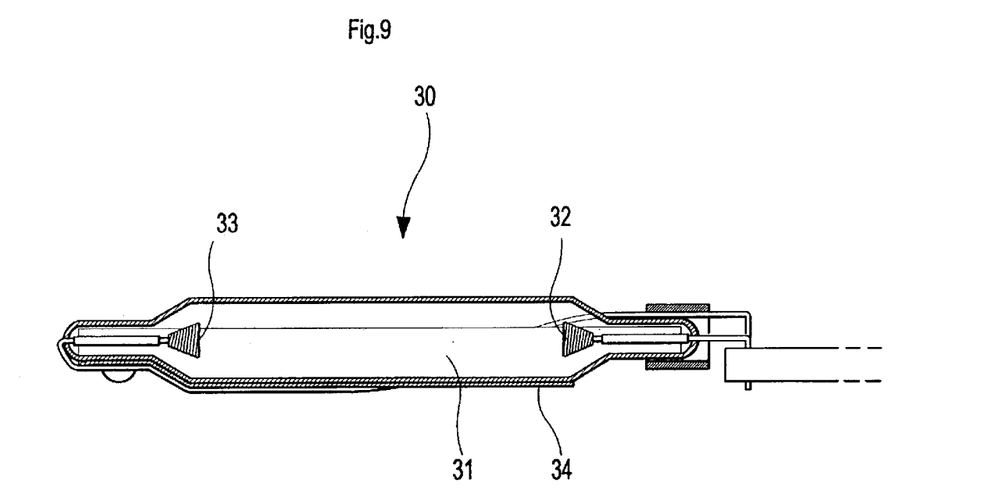
FIG. 9 is a view, partly in cross section, of radiation means in the toothbrush case according to the present invention.
Figure 10:
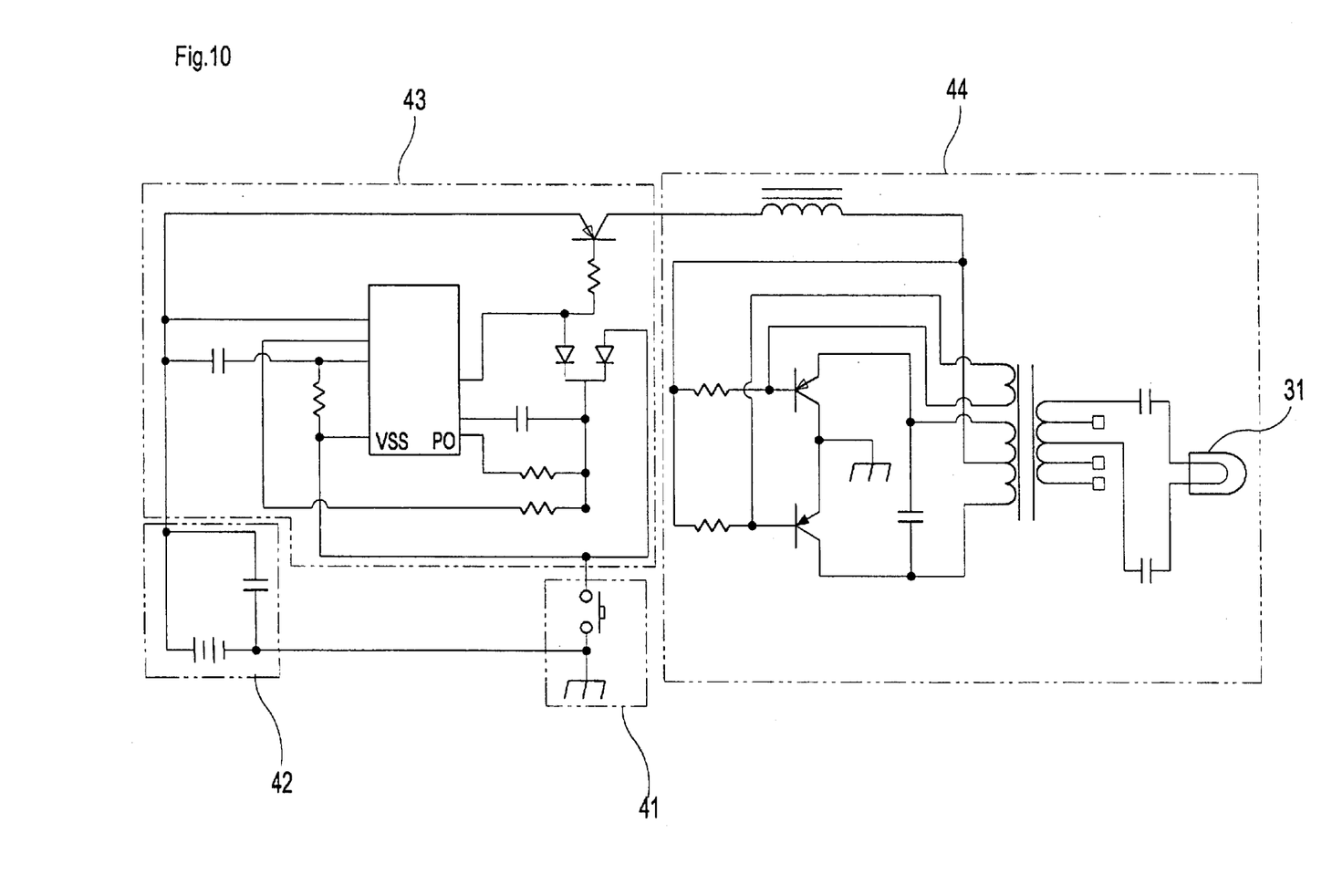
FIG. 10 is a circuit diagram of the toothbrush case according to the present invention.

As shown in FIG. 8, a spaced projection 54 is formed immediately below the part of the UV discharging outlet 52 of the receiving member 50 to sanitize bacteria penetrated into the bristles 110 of the toothbrush 100 by UV light radiated through the outlet 52. By this projection 54, the toothbrush case is spaced from the bottom surface of the receiving member 50.

Both sides of the receiving member 50 is provided with an engagement projection 55 which can engage with an engagement groove 27 of the lower case 20 so that the receiving member 50 can fixedly engage with the lower case 20 when the receiving member 50 engages with the lower case 20.

On the other hand, the numeral 60 is an upper case hinge-coupled with the lower case 20, the upper case 60 is an injection molded by a transparent material so that it can be confirmed whether the toothbrush 100 is contained within the toothbrush case or not.

Also, the upper surface of the upper case is provided with a top air flow path 62 flowing air in order not to generate fog in the inside of the upper case 60 due to the moisture left in the toothbrush, thus sterilizing the toothbrush 100 more effectively without reduction of the UV intensity.

Figure 3:
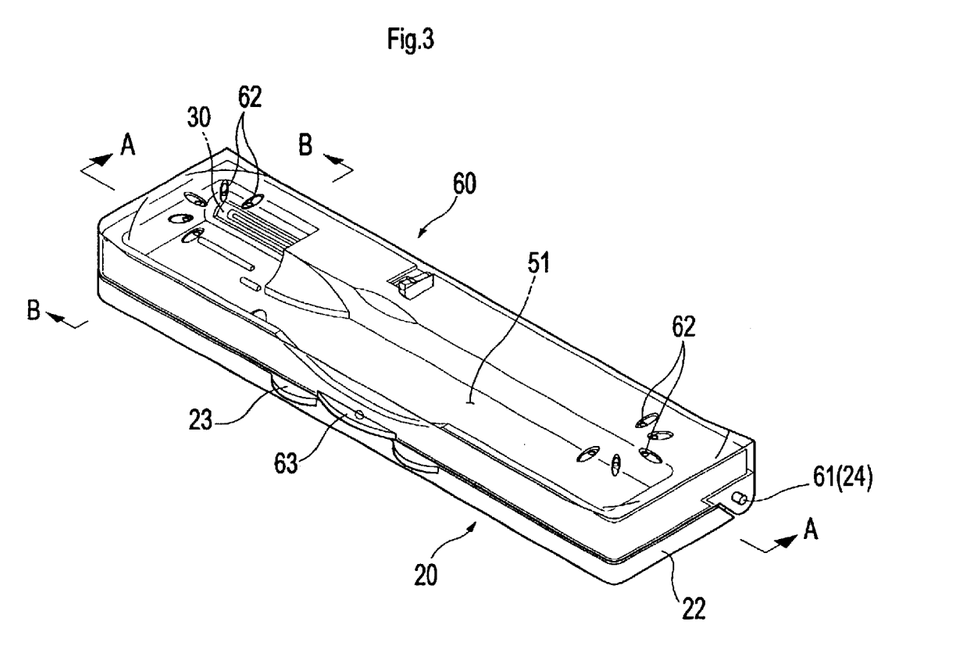
FIG. 3 is a perspective view showing the toothbrush case according to the present invention.
Figure 4:
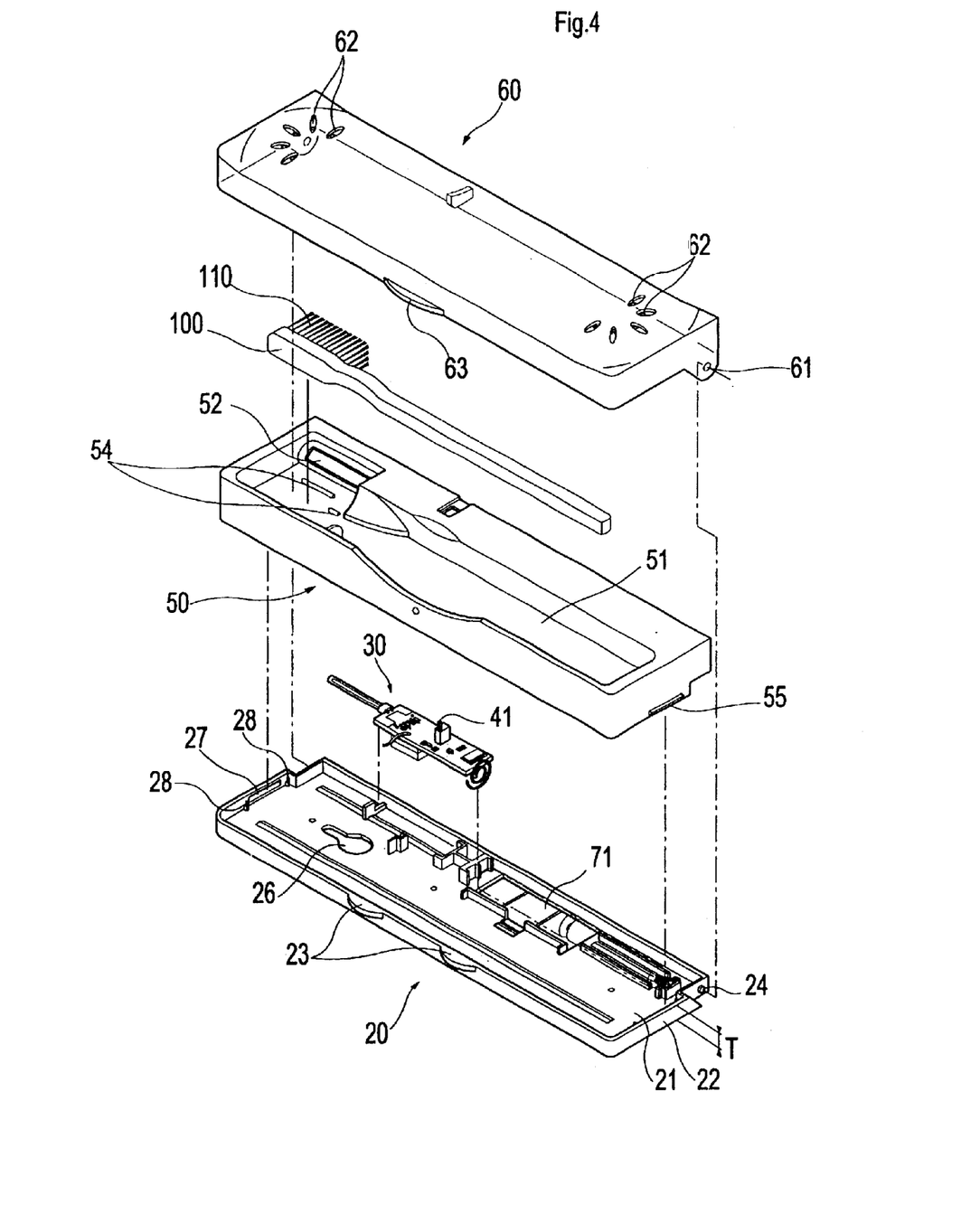
FIG. 4 is an exploded perspective view showing main components of the toothbrush case according to the present invention taken from an upper part.
Figure 12:
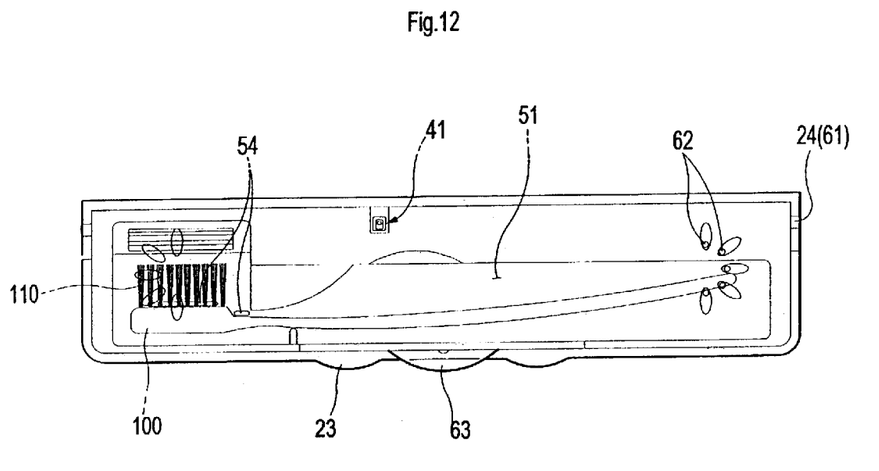
FIG. 12 is a plan view of the toothbrush case according to another embodiment of the present invention.

Also, as shown in FIG. 12, the top airflow path 62 is desirably positioned on the opposing position of the bristle 110 of the toothbrush 100 to prevent air from flowing into the bristle 110. The present invention is not limited to the this structure and can be applied to any structure which can flow outside air into the inside of the upper case 60 as is shown in FIGS. 3 to 5.

The rear side of the upper case 60 is provided with a hinge hole 61 engaged with a hinge projection portion 24 in the lower case 20 in order to open or close the receiving member 50.

The front center in the upper case is provided with a top projection portion 63 in order to open or close the upper case 60.

Next, the functional effect for the toothbrush case according to the present invention is described.

Firstly, since the receiving member 50 according to the invention is an injection molded with photocatalyst such as TiO2 which can eliminate bad smells, bacteria, and mold through a strong oxidation-reduction reaction by the UV light radiated from the UV radiation means 30 for an organic material in an environment, or is coated by spraying photocatalyst such as TiO2 onto the antimicrobial ABS resin, it is possible to double the antibacterial and deodorant effect.

Also, since the spaced supporting portion 25 is projected at a given height M on the bottom of the supporting surface 21 in the lower case 20, even if the lower case 20 is placed on the ground such as bathroom's ground, the supporting surface 21 is spaced from the ground at the given height M, preventing moisture flowing into the inside of the lowercase 20. Moreover, the lower case 20 can be picked up easily from a wet place because surface tension does not occur at the interface between the ground and the lower case by the spaced supporting portion 25.

When the toothbrush 100 is received in the receiving portion 51 of the receiving member 50, the lower case 20 of the toothbrush 100 is spaced by the bottom surface of the receiving portion 51, thus doubling the sterilization effect by radiating UV radiation from the UV radiation means 30 to the bristle 110.

After the toothbrush 100 is received in the receiving member 50, if the upper case 60 is closed, moisture left on the bristle 110 of the toothbrush 100 can be exhausted to the outside through the lower air flow path 26 in the lower case 20 and the upper air flow path 62 in the upper case 60.

Also, since the moisture left in the bristle of the toothbrush 100 can be exhausted through the lower air flow path 26 in the lower case 20 and the upper air flow path 62 in the upper case 60, it is possible to keep the surface of the upper case 60 clean, and to double the effect of sterilization by radiating UV light radiated from the UV radiation means 30 to the toothbrush 100.

If the toothbrush 100 is positioned in the toothbrush case and the upper case 60 is closed, the toothbrush 100 can be sterilized in the power saving mode within the toothbrush case according to the present invention.

If the upper case 60 is closed, the sensor 41 senses it and a low voltage is applied to the power supply initially under the control of the control member 40. The voltage is applied to the condenser member 34, and UV is radiated from the lamp 31 by discharging gas mixed between the condenser member 34 and the first W filament coil 32, one end of the condenser being coupled to the second W filament coil 33, the other end of the condenser being coupled to the top of the first W filament coil 32.

The control member 40 can operate with an operation acknowledgement mode 300 for turning on the lamp 31 for one minute then turning it off in order to detect whether lamp 31 operates correctly or not, and a power saving acknowledgement mode 400 for turning on the lamp 31 for three minutes each hour in power saving mode after the operation acknowledgement mode 300 is executed in order to radiate UV effectively in the power saving mode.

As mentioned above, according to the structure of the toothbrush of the present invention, since outside air flows through the lower air flow path in the lower case and the upper air flow path in the upper case, it is possible to exhaust moist left in the bristle of the toothbrush with air outside of the toothbrush case and to prevent fog from generating inside the toothbrush case.

Also, in case that the toothbrush case is placed on a wet place, due to the spaced support formed at the lower case, it is possible to prevent moist from penetrating into the inside of the case and the case can be picked up easily since the surface tension between the case and the bottom surface is decreased even if the case is placed on the ground.

Also, the toothbrush case of the present invention has advantages that it can save power consumption largely by radiating UV in the power saving mode and by operating the UV radiation means in a timely manner.

What is claimed is:

1. A toothbrush case comprising a lower case having a projection portion for projecting at a given height (T) on a supporting surface, an ultraviolet radiation means supported by the supporting surface in the lower case, a receiving member having a portion for receiving a toothbrush in order to sanitize said toothbrush with ultraviolet light radiated by the ultraviolet radiation means, an ultraviolet discharging outlet, and an upper case being hinge coupled with the lower case for opening and closing the receiving member, the toothbrush case further comprising:
   a spaced supporting portion being provided on a lower surface of the supporting surface in the lower case and being projected at the given height (T) so that ground moisture does not contact with the supporting surface and that outside air flows into a bottom of the supporting surface when the lower case is placed on the ground;
   a lower air flow path being formed on the supporting surface in the lower case so that outside air flows into an inside of the lower case through a space created by the spaced supporting portion;
   an air flow path provided between the ultraviolet radiation means and an ultraviolet discharging outlet of the receiving member so that outside air flows through the lower air flow path into a sealing space between the receiving member and the upper case, and
   an upper airflow path provided on the upper case so that outside air flows through the upper case into the receiving member having the air flow path.

2. A toothbrush case according to claim 1 wherein the receiving member comprises a photocatalyst in order to cause a strong oxidation-reduction reaction for environmental organic material, and to eliminate bad smells, bacterium, and mold.

3. A toothbrush case according to claim 1 wherein a spaced projection portion is formed in front of the UV discharging outlet of the receiving member to sanitize bacteria penetrated into a bristle by using UV light radiated through the outlet.

4. A toothbrush case according to claim 1 wherein the upper airflow path is positioned in opposing position with a bristle of the toothbrush to prevent dust from flowing into the bristle.

5. A toothbrush case according to claim 2, wherein the photocatalyst is TiO2.

6. An UV sanitizing toothbrush case for sanitizing a toothbrush by UV radiation comprising;
   a lower case having a spaced supporting portion formed on a lower surface of a supporting surface, and a portion for projecting on the surface at a given height (T), the surface is provided with a lower air flow path, thus flowing in air through the lower air flow path formed by the spaced supporting portion;
   a receiving member having a receiving portion being engaged with the lower case for receiving the toothbrush and having an UV discharging outlet, the member is sprayed and coated with photocatalyst to cause strong oxidation-reduction reaction for environmental organic material in order to eliminate bad smells, bacteria, and mold;
   an upper case having an upper air flow path thereon, for hinge-coupling with the lower case to close the receiving member after the toothbrush is received in the receiving portion of the receiving member; and
   an UV radiation means provided between the receiving member and the lower case for radiating UV light to the toothbrush for sterilization by UV and for turning on a UV lamp promptly in a power saving mode in case that the upper case is closed.

7. An UV sanitizing toothbrush case according to claim 6 wherein the UV radiation means includes:
   a lamp made of a transparent crystal material having high transmissivity, and sealed with gas mixed with inert gas;
   a first and a second W filament coils provided on both ends of the lamp and covered with BaO2 thereon so that hot electrons can be emitted easily from mixed gas in the lamp;
   a condenser made of high conductive material, wherein one end of the condenser is coupled to the second W filament coil, and the other end of the condenser is coupled to the top of the first W filament coil in order to emit hot electron gas even if a low voltage is applied to the first and the second W filament coil; and
   a control member for controlling hot electron emission and UV light radiation by the condenser under the low voltage.

8. An UV sanitizing toothbrush case according to claim 7 wherein if the low voltage is applied initially to the toothbrush case under control of the control member, the voltage is applied to the condenser, one end of the condenser being coupled to the second W filament coil, and the other end of the condenser being coupled to the top of the first W filament coil so that UV light is emitted from the lamp by discharging the mixed gas between the condenser member and the first W filament coil.

9. An UV sanitizing toothbrush case according to claim 7 wherein in order to sanitize the toothbrush effectively by UV radiated from the lamp, the control member comprises a sensor for detecting when the toothbrush is positioned in the toothbrush case and the upper case is closed;
   a power supply for providing power responsive to a sense signal of the sensor;

a controlling portion for controlling power supplied from the power supply in the power saving mode; and a voltage output for outputting regular voltage to the W filament coils so that the voltages supplied from the power supply responsive to a control signal of the controlling portion output at rating voltage.

10. An UV sanitizing toothbrush case according to claim 9 wherein the control member can operate with an operation acknowledgement execution mode for turning on the lamp for one minute then turning it off in order to know whether the lamp operates correctly or not, and a power saving acknowledgement mode for turning on the lamp three minutes per hour in the power saving mode after the operation acknowledgement mode is executed in order to radiate UV effectively.

11. A toothbrush case according to claim 6, wherein the photocatalyst is an ABS resin.

* * * * *